United States Patent
Aiertza Otxotorena et al.

(10) Patent No.: US 10,550,205 B2
(45) Date of Patent: Feb. 4, 2020

(54) PROCESS FOR PREPARING WATER-DISPERSIBLE SINGLE-CHAIN POLYMERIC NANOPARTICLES

(71) Applicant: FUNDACIÓN CIDETEC, Donostia-San Sebastián (ES)

(72) Inventors: Miren Karmele Aiertza Otxotorena, Donostia-San Sebastián (ES); Laura Sánchez Abella, Donostia-San Sebastián (ES); Ana Belén Benito Collado, Donostia-San Sebastián (ES); Iraida Loinaz Bordonabe, Donostia-San Sebastián (ES); Germán Cabañero, Donostia-San Sebastián (ES); Hans-Jürgen Grande, Donostia-San Sebastián (ES); Marco Marradi, Donostia-San Sebastián (ES); Raquel Gracia España, Donostia-San Sebastián (ES)

(73) Assignee: FUNDACIÓN CIDETEC, Donostia-San Sebastián (ES)

( * ) Notice: Subject to any disclaimer, the term of this patent is extended or adjusted under 35 U.S.C. 154(b) by 0 days.

(21) Appl. No.: 15/520,809

(22) PCT Filed: Nov. 2, 2015

(86) PCT No.: PCT/EP2015/075404
§ 371 (c)(1),
(2) Date: Apr. 20, 2017

(87) PCT Pub. No.: WO2016/071258
PCT Pub. Date: May 12, 2016

(65) Prior Publication Data
US 2017/0320974 A1 Nov. 9, 2017

(30) Foreign Application Priority Data
Nov. 3, 2014 (EP) ..................... 14382433

(51) Int. Cl.
C08F 8/32 (2006.01)
A61K 49/00 (2006.01)
A61K 49/18 (2006.01)
A61K 47/69 (2017.01)
C08G 75/12 (2016.01)

(52) U.S. Cl.
CPC ............ *C08F 8/32* (2013.01); *A61K 47/6933* (2017.08); *A61K 47/6939* (2017.08); *A61K 49/0093* (2013.01); *A61K 49/1818* (2013.01); *C08G 75/12* (2013.01)

(58) Field of Classification Search
CPC .......... C08F 8/32; C08F 220/34; C08G 75/12; A61K 47/6939; A61K 47/6933; A61K 49/1818; A61K 49/0093
See application file for complete search history.

(56) References Cited

FOREIGN PATENT DOCUMENTS

WO WO 2003/022910 3/2003

OTHER PUBLICATIONS

International Search Report and Written Opinion of the International Searching Authority dated Feb. 4, 2016 for PCT/EP2015/075404, 12 pages.
Ryu, Ja-Hyoung, et al. "Surface-functionalizable Polymer Nanogels with Facile Hydrophobic Guest Encapsulation Capabilities", Journal of the American Chemical Society, Jun. 23, 2010 vol. 132, No. 24, pp. 8246-8247.

*Primary Examiner* — Robert S Cabral
(74) *Attorney, Agent, or Firm* — Squire Patton Boggs (US) LLP (57) ABSTRACT

The present invention comprises a process for preparing water-dispersible single-chain polymeric nanoparticles, which comprises cross-linking a polymer having a solubility equal to or higher than 100 mg per litre of water, and an amount of complementary reactive groups comprised from 5 to 60 molar % of the total amount of monomer units present in the polymer chain; with a crosslinking agent having crosslinkable groups; at a temperature comprised from 20 to 25° C. in the absence of a catalyst; to obtain water-dispersible conjugates and compositions containing the nanoparticle; and the use thereof.

11 Claims, 1 Drawing Sheet
Specification includes a Sequence Listing.

PROCESS FOR PREPARING WATER-DISPERSIBLE SINGLE-CHAIN POLYMERIC NANOPARTICLES

The present invention relates to the field of nanoparticles and more particularly to the field of the preparation of nanoparticles. Especially, it relates to a process for the preparation of water-dispersible, single-chain polymeric nanoparticles. The invention also relates to those nanoparticles obtained by that process, water-dispersible conjugates containing those nanoparticles, as well as their use in biomedicine.

BACKGROUND ART

Nanoparticles are tiny particles which sizes are less than 100 nm and have many industrial applications due to their novel physical and chemical properties. Some of those applications are in the field of nanobiotechnology, drug delivery, catalysis, fluorescent biological labels, biodetection of pathogens, chemical sensors, optical/electronic/magnetic devices, and medicine.

The development of a large number of synthetic techniques has permitted the use of many different types of materials to obtain very diverse sizes of nanoparticles, from hundreds down to just a few nanometers. However, the main concern of using nanoparticles in nanomedicine is their potential toxicity for living systems mainly derived from accumulation in different tissues and organs.

It is known that the exhibited physical and chemical properties of the nanoparticles are often size-dependent. Several approaches for the synthesis of controlled-molar mass and narrow size distribution to guarantee the uniformity of the resulting nanoparticles as much as possible in a large scale have been developed. One of these approaches comprises the use of the click reaction chemistry.

A reaction process needs to comply with the following requirements to be classified as a click reaction process: to have a single-reaction trajectory; to be chemoselective; to be wide in scope (i.e., applicable under a broad range of conditions with a multitude of starting substrates); to be modular; to give stable compounds; and to show high yields. Additional requirements for reactions involving one or more polymeric reagents to be classified as click reactions are: to operate in fast time-scales; and to proceed with equimolarity.

Three different methods have been developed for single-chain nanoparticle construction via click chemistry: intrachain homocoupling, intrachain heterocoupling, and cross-linker-induced collapse. Particularly, the crosslinker-induced collapse process involves the addition of a crosslinker to generate intra-molecular crosslinking of a single polymeric chain to give discrete single-chain polymeric nanoparticles via click chemistry. The reaction comprises the linkage of the crosslinkable groups of the cross-linking agent with the complementary reactive groups of the polymer chain. The size of the resulting nanoparticles is accurately controlled by either the initial degree of polymerization of the polymeric precursor or the level of incorporation of the crosslinking agent.

Even though the efficiency of this technique has been recognized, this strategy suffers from some drawbacks. One of these drawbacks is the generation of by-products obtained by the undesired inter-molecular crosslinking reaction between different polymeric chains. To avoid these undesired inter-molecular reactions, the use of ultra-dilute reaction conditions are required. However, these conditions compromise the viability of the large scale synthesis of nanoparticles using this process and does not ensure that the inter-molecular cross-linking reactions are entirely avoided.

Additional drawbacks of the above mentioned synthetic click processes are the demanding experimental reaction conditions required. For instance, the use of organic solvents, and the use of catalysts limit their broad use at a large scale because further puryfing and refinements steps are required. Additionally, either starting materials such as polymeric precursors, crosslinking agent, and/or obtained nanoparticles can be incompatible with the experimental conditions required in the reaction.

Other processes for the preparation of single-chain polymeric nanoparticles have been disclosed in the state of the art. These processes are carried out under high temperatures. The use of high temperatures is a drawback for their industrial scale-up.

Therefore, several improvements for carrying out the above crosslinker-induced collapse reaction process under mild conditions have been disclosed in the state of the art. The reduction of the temperature and/or the removal of organic solvents and catalyst have been studied.

However, it is disclosed in the state of the art that the temperature is a critical parameter to obtain nanoparticles. Additionally, the requirements of severe anhydrous reaction medium for carrying some of the above mentioned click reactions due to the presence of water-incompatible catalysts/initiators limit the industrial production of single-chain polymeric nanoparticles.

Therefore, from what is known in the art, it is derived that there is still the need of providing a scale-up process for the preparation of water-soluble nanoparticles under mild conditions.

SUMMARY OF THE INVENTION

Inventors have found a simple scale-up process for preparing water-dispersible nanoparticles having a controlled reduced particle size maintaining the polydispersion of the polymer chain precursor. The process of the invention also allows increasing the intramolecular crosslinking reaction to yield well-defined nanoparticles with no or a minimal amount of inter-molecular coupling reactions between polymeric chains. The control of the particle size and polydispersion of the water-dispersible nanoparticles is achieved by the selection of the appropriate polymer chain precursor having an appropriate solubility in water, in combination with the mild experimental conditions. The mild conditions imply the use of an aqueous medium and carrying out the process at room temperatures under a high dilution system resulted from the controlled, slow and continuous addition of the crosslinking agent to the polymer (or viceversa). It is advantageous because the process of the invention allows obtaining water-dispersible nanoparticles in the absence of organic solvents and polymerization or cross-linking catalysts.

Thus, the first aspect of the present invention relates to a process for preparing water-dispersible single-chain polymeric nanoparticles, which comprises cross-linking a polymer having a solubility equal to or higher than 100 mg per litre of water, and an amount of complementary reactive groups comprised from 5 to 60 molar % of the total amount of monomer units present in the polymer chain; with a homobifunctional crosslinking agent having crosslinkable groups; by (a) Adding an aqueous solution of the polymer to an aqueous solution of the homobifunctional crosslinking agent at an addition rate that allows having during the addition of the polymer a concentration of the crosslinkable groups of the polymer in the solution of the homobifunctional crosslinking agent comprised from $10^{-3}$ to $10^{-7}$ molar; or alternatively, (a') Adding an aqueous solution of the homobifunctional crosslinking agent to an aqueous solution of the polymer at an addition rate that allows having during the addition of the homobifunctional crosslinking agent a concentration of the homobifunctional crosslinking agent in the solution of the polymer comprised from $10^{-3}$ to $10^{-7}$ molar; at a temperature comprised from 20 to 25° C. in the absence of a catalyst; wherein the water-dispersible single-chain polymeric nanoparticles have a particle size comprised from 3 to 30 nm and a polydispersion of the particle equal to the polydispersion of the polymer ±20%.

The second aspect of the present invention relates to the water-dispersible single-chain polymeric nanoparticles obtainable by the process as defined in the first aspect of the invention.

The third aspect of the invention relates to a water-dispersible conjugate, which comprises the water-dispersible single-chain polymeric nanoparticles as defined in the first or the second aspect of the invention, and at least an active agent.

The fourth aspect of the invention relates to a pharmaceutical or diagnostic composition which comprises the water-dispersible conjugate as defined in the third aspect of the invention, together with one or more appropriate pharmaceutically or diagnostically acceptable excipients or carriers.

The fifth aspect of the invention relates to a kit comprising the water-dispersible conjugate as defined in the third aspect of the invention.

The sixth aspect of the invention relates to the water-dispersible conjugate as defined in the third aspect of the invention, for use in therapy when the active agent is an active ingredient.

The seventh aspect of the invention relates to the use of the water-dispersible conjugate as defined in the third aspect of the invention, wherein the active agent is an imaging agent for use as an imaging agent.

The eighth aspect of the invention relates to the water-dispersible conjugate as defined in the third aspect of the invention for use in diagnostics.

Finally, the ninth aspect of the invention relates to the use of the water-dispersible single-chain polymeric nanoparticles as defined in the first and the second aspect of the invention as a carrier.

DETAILED DESCRIPTION OF THE INVENTION

All terms as used herein in this application, unless otherwise stated, shall be understood in their ordinary meaning as known in the art. Other more specific definitions terms as used in the present application are as set forth below and are intended to apply uniformly throughout the specification and claims unless an otherwise expressly set out definition provides a broader definition.

The term "water-dispersible" refers to a single-chain polymeric nanoparticle whose dispersability in water is equal to or greater than 100 mg per litre of water. The term "dispersability" refers to the capacity of the single-chain polymeric nanoparticle of the present invention to be uniformly dispersed in water and can be filtered through a 0.2 micron size filter.

The term "aqueous solution" refers to a solution which contains minimum 50 wt % of pure water.

The term "polymer" refers to molecules formed from the chemical union of two or more repeating monomers. Accordingly, the term "polymer" includes homopolymers (prepared from two or more equal monomers), and copolymers (prepared from two or more different monomers). The terms "polymer", "precursor polymer", "linear polymer" and "polymer coil" have the same meaning and are used interchangeable. These terms refers to the polymer that is used as a starting material for the preparation of the nanoparticles of the present invention. The polymer may be synthetic, natural or semisynthetic. The term "polymer" refers to molecules which have a molecular weight (MW) greater than 10,000 Da; preferably comprised from 10,000 to 100,000 Da; more preferably from 20,000 to 50,000 Da. The term "synthetic polymer" refers to those polymers that are not naturally occurring and that are entirely produced via chemical synthesis. The term "natural polymer" refers to those polymers that are naturally occurring polymers. The term "semisynthetic polymer" refers to those natural polymers that have been chemically modified via chemical synthesis.

The polymers used in the present invention have a solubility equal to or higher than 100 mg per litre of water. The solubility of the polymers of the invention can be measured by any method disclosed in the state of the art for measuring the solubility of polymers. In particular, in the present invention the solubility has been determined measuring visible light transmitance which has to be 100% for those completely dissolved polymers.

The polymers used in the present invention contain an amount of complementary reactive monomers comprised from 5 to 60 molar % of the total amount of monomer units present in the polymer chain. The term "complementary reactive groups" refers to those functional groups of the polymer that allow forming a three-dimensional crosslinked nanoparticle (network) with the crosslinkable groups of the crosslinking agent. The "complementary reactive groups" can be forming part of the backbone of the polymer, or can be attached to the backbone as lateral chains.

The term "polydispersion of a polymer" refers to the "polydispersity of a polymer" a value calculated by dividing the weight average molecular weight of the polymer by the number average molecular weight. This value means the range of molecular weights present in the polymer and refers to the broadness molecular weight distribution obtained from size exclusion chromatography (SEC) analysis.

The term "polydispersion of the particle size of the nanoparticle" refers to "polydispersity of the particle size" a value obtained from the square of the standard deviation divided by the mean diameter. The polydispersity of the particles size refers to the broadness of the size distribution obtained by Dynamic Light Scattering (DLS).

Those "complementary reactive groups" can be forming part of the structure of the polymer or they can be introduced in the structure of the polymer. When the complementary reactive groups are introduced, this step can be carried out in several steps, either during the polymerization step or when the polymerization process has already finished. In a particular embodiment, the addition of the "complementary reactive groups" is carried out by a trans-esterification of a hydroxyl group of a polysaccharide chain with glycidyl-methacrylate.

The term "crosslinked" refers to a nanoparticle that have three-dimensional crosslink network wherein the network is formed by a single-chain of the starting polymer which has been collapsed by one or more crosslinking agents.

The term "crosslinking" refers in the polymer science field to the use of cross-links to promote a difference in the physical properties of the polymers. The term "crosslink" refers to bonds that link one "complementary reactive group" with a crosslinkable group of the crosslinking agent by covalent bonding. For example, the bond that link one "complementary reactive group" of the single-chain of the polymer with a crosslinkable group of the crosslinking agent by covalent bonding, or viceversa. The term "crosslinker" or "crosslinking agent" which is herein used interchangeably refers to compound having the ability to cross-link polymer chain(s). The term "homobifunctional crosslinking agent" refers to those crosslinking agents that contain two identical reactive sites (i.e. two identical crosslinkable groups), which can react with the complementary reactive groups.

The term "cross-linkable monomer" or "reactive monomer", or "complementary monomer" which is herein used interchangeably refers to the functional group on the polymer chain that reacts with the crosslinker to form the single-chain polymeric nanoparticles.

The term "pharmaceutically acceptable" refers to those excipients or carriers suitable for use in the pharmaceutical technology for preparing compositions with medical use.

The term "diagnostically acceptable" refers to those excipients or carriers suitable for use in the diagnostic technology for preparing compositions with diagnostic use. In particular, the term "diagnostically imaging acceptable" refers to excipients or carriers suitable for use in the imaging diagnostic technology for preparing compositions with imaging diagnostic use.

In an alternative embodiment, the process of the invention is carried out at an addition rate that allows having during the addition of the polymer a concentration of the crosslinkable groups of the polymer in the solution of the homobifunctional crosslinking agent comprised from $10^{-3}$ to $10^{-7}$ molar (process a). In an alternative embodiment, the process of the invention is carried out at an addition rate that allows having during the addition of the homobifunctional crosslinking agent a concentration of the homobifunctional crosslinking agent in the solution of the polymer comprised from $10^{-3}$ to $10^{-7}$ molar (process a').

In a preferred embodiment, the concentration of the crosslinkable groups of the polymer in the solution of the homobifunctional crosslinking agent, or alternatively, the concentration of the homobifunctional crosslinking agent in the solution of the polymer is comprised from $10^{-4}$ to $10^{-6}$ molar; more preferably about $10^{-5}$ molar. The addition rate in combination with the other experimental conditions mentioned above allows preparing nanoparticles with the appropriate physical and chemical properties for being used in biomedicine.

In an embodiment, optionally in combination with one or more features of the various embodiments described above or below, the process for preparing water-dispersible single-chain polymeric nanoparticles, which comprises cross-linking a polymer having a solubility equal to or higher than 100 mg per litre of water, and an amount of complementary reactive groups comprised from 5 to 60 molar % of the total amount of monomer units present in the polymer chain; with a homobifunctional crosslinking agent having crosslinkable groups; by (a) Adding an aqueous solution of the polymer to an aqueous solution of the homobifunctional crosslinking agent at an addition rate that allows having during the addition of the polymer a concentration of the crosslinkable groups of the polymer in the solution of the homobifunctional crosslinking agent comprised from $10^{-3}$ to $10^{-7}$ molar; at a temperature comprised from 20 to 25° C. in the absence of a catalyst; wherein the water-dispersible single-chain polymeric nanoparticle has a particle size comprised from 3 to 30 nm and a polydispersion of the particle equal to the polydispersion of the polymer ±20%.

In an alternative embodiment, optionally in combination with one or more features of the various embodiments described above or below, the process for preparing water-dispersible single-chain polymeric nanoparticles, which comprises cross-linking a polymer having a solubility equal to or higher than 100 mg per litre of water, and an amount of complementary reactive groups comprised from 5 to 60 molar % of the total amount of monomer units present in the polymer chain; with a homobifunctional crosslinking agent having crosslinkable groups; by (a') Adding an aqueous solution of the homobifunctional crosslinking agent to an aqueous solution of the polymer at an addition rate that allows having during the addition of the homobifunctional crosslinking agent a concentration of the homobifunctional crosslinking agent in the solution of the polymer comprised from $10^{-3}$ to $10^{-7}$ molar; at a temperature comprised from 20 to 25° C. in the absence of a catalyst; wherein the water-dispersible single-chain polymeric nanoparticle has a particle size comprised from 3 to 30 nm and a polydispersion of the particle equal to the polydispersion of the polymer ±20%.

In an embodiment of the invention, optionally in combination with one or more features of the various embodiments described above or below, the process is that wherein the water-dispersible single-chain polymeric nanoparticles have a polydispersion of the particle equal to the polydispersion of the polymer ±15%; preferably ±10%; more preferably ±5%.

In an embodiment of the invention, optionally in combination with one or more features of the various embodiments described above or below, the process is that wherein the water-dispersible single-chain polymeric nanoparticles have a particle size comprised from 5 to 20 nm and a polydispersion of the particle equal to the polydispersion of the polymer ±20%.

The process of the invention is carried out with a polymer having an amount of complementary reactive groups comprised from 5 to 60 molar % of the total amount of monomer units present in the polymer chain. In an embodiment, optionally in combination with one or more features of the various embodiments described above or below, the process is carried out with a polymer having an amount of complementary reactive groups comprised from 10 to 40 molar % of the total amount of monomer units present in the polymer chain.

The process of the invention is that wherein the single-chain polymeric nanoparticles have a particle size comprised from 3 to 30 nm; with a polydispersion of the particle equal to the polydispersion of the polymer ±20%. In an embodiment, optionally in combination with one or more features of the various embodiments described above or below, the process is carried out with a polymer having an amount of complementary reactive groups comprised from 5 to 60 molar % of the total amount of monomer units present in the polymer chain; more preferably comprised from 10 to 40 molar % of the total amount of monomer units present in the polymer chain. The particle size of the nanoparticles of the invention and their polydispersion can be measured by any method disclosed in the state of the art for measuring the particle size of nanoparticles. In particular, the method used in the present invention for measuring the particle size in solution is Dynamic light scattering (DLS) reporting the number average diameter value and Atomic force microscopy (AFM) or transmission electron microscopy (TEM) to measure dried particles and the method used in the present invention for measuring the polydispersion of the particle of the nanoparticles is size exclusion chromatography (SEC).

In an embodiment, optionally in combination with one or more features of the various embodiments described above or below, the process is that wherein the percentage of intramolecular crosslinking of the nanoparticle is comprised from 3 to 45 molar % of the total amount of monomer units present in the polymer chain of the nanoparticle; preferably comprised from 5 to 20 molar % of the total amount of monomer units present in the polymer chain.

In an embodiment, optionally in combination with one or more features of the various embodiments described above or below, the process comprises reacting a polymer having an amount of complementary reactive groups comprised from 10 to 40 molar % of the total amount of monomer units present in the polymer chain; and the single-chain polymeric nanoparticles have a particle size comprised from 3 to 20 nm, and a percentage of intramolecular crosslinking comprised from 5 to 20 molar % of the total amount of monomer units present in the polymer chain.

In an embodiment, optionally in combination with one or more features of the various embodiments described above or below, in the process of the invention, the polymer is a copolymer. Examples of copolymers appropriate for the present invention include, but are not limited to, methacrylate copolymers, acrylate-methacrylate copolymers, or acrylamide copolymers, for instance poly[(metha)acrylic acid-co-2-(2-(aminooxy)acetamido)ethyl methacrylate], and poly[N,N-dimethyl-2-aminoethylmethacrylate-co-2-(aminooxy)ethyl methacrylate].

In an alternative embodiment, optionally in combination with one or more features of the various embodiments described above or below, in the process of the invention, the polymer is a semi-synthetic polymer derived from a natural polymer. Examples of natural polymers appropriate for the preparation of the semi-synthetic appropriate for the present invention include, but are not limited to, dextran, alginate, chitosan, and hyaluronic acid. Examples of semi-synthetic polymer appropriate for the present invention include glycidyl methacrylate derivatized dextran or hyaluronic acid.

In an embodiment, optionally in combination with one or more features of the various embodiments described above or below, in the process of the invention, the complementary reactive group of the polymer of the invention is —O—C(=O)—C(=CH$_2$)—CH$_3$ group; the crosslinkable group of the homobifunctional crosslinking agent is —SH group; and the process is carried out at a pH equal to or higher than 8. In an alternative embodiment, optionally in combination with one or more features of the various embodiments described above or below, in the process of the invention the complementary reactive group of the polymer is a —SH group, the crosslinkable group of the homobifunctional crosslinking agent is a —O—C(=O)—C(=CH$_2$)—CH$_3$ group, and the process is carried out at a pH equal to or higher than 8.

In an embodiment, optionally in combination with one or more features of the various embodiments described above or below, in the process of the invention, the complementary reactive group of the polymer of the invention is —O—NH$_2$ group; the crosslinkable group of the homobifunctional crosslinking agent is a —CHO group; and the process is carried out at a pH comprised from 5 to 7. In an alternative embodiment, optionally in combination with one or more features of the various embodiments described above or below, in the process of the invention, the complementary reactive group of the polymer is a —CHO group, the crosslinkable group of the homobifunctional crosslinking agent is a —O—NH$_2$ group, and the process is carried out at a pH comprised from 5 to 7.

In an embodiment, optionally in combination with one or more features of the various embodiments described above or below, the process of the invention further comprises a previous step of submitting a polymer with protected complementary reactive groups to a de-protection reaction to yield the polymer having the de-protected complementary reactive groups as defined above. The de-protection reaction can comprise submitting the polymer with the protected complementary reactive groups to acidic conditions, basic conditions or any other suitable de-protection condition.

In an embodiment, optionally in combination with one or more features of the various embodiments described above or below, the process of the invention further comprises a previous step of submitting a crosslinking agent with protected crosslinkable groups to a de-protection reaction to yield the crosslinking agent with de-protected crosslinkable groups as defined above. The de-protection reaction can comprise submitting the crosslinking agent with the protected crosslinkable groups to acidic conditions, basic conditions or any other suitable deprotection condition.

In an embodiment, optionally in combination with one or more features of the various embodiments described above or below, the process of the invention further comprises a previous step of submitting a polymer with protected complementary reactive groups to a de-protection reaction to yield the polymer having the de-protected complementary reactive groups as defined above; and submitting a crosslinking agent with protected crosslinkable groups to a de-protection reaction to yield the crosslinking agent with de-protected crosslinkable groups as defined above.

In an embodiment, optionally in combination with one or more features of the various embodiments described above or below, in the process of the invention wherein the water-dispersible single-chain polymeric nanoparticle as defined above or below have reactive functional groups, the process further comprises an additional step of converting the reactive functional groups into non-reactive functional groups. It is advantageous because those modifications can improve some physical and/or chemical properties of the nanoparticles such as for example their lifetime, or their stability. Appropriate modifications of the structure of the nanoparticle can be covalent linkage of polyethyleneglycol chain, the covalent linkage of a peptide, the incorporation of positive or either negative charged functional groups, and the linkage of hydroxyl groups, and low molecular weight alcanes.

In an embodiment, optionally in combination with one or more features of the various embodiments described above or below, the process of the invention further comprises an additional step of purifying the nanoparticle obtained in the process as defined above and below. Any method appropriate for purifying the nanoparticle disclosed in the state of the art can be used. In particular, the purifying step is selected from the group consisting of dialysis, centrifuge filtration and precipitation; preferably, the purifying step is carried out by dialysis.

In an embodiment, optionally in combination with one or more features of the various embodiments described above or below, the process of the invention further comprises an additional step of drying the nanoparticle as defined above or below. Any method appropriate for drying the nanoparticle disclosed in the state of the art can be used. In particular, the drying step is selected from the group consisting of spray drying, and freeze-drying. In a preferred embodiment, the drying step carried out is freeze-drying.

In an embodiment, optionally in combination with one or more features of the various embodiments described above or below, the process of the invention further comprises additional steps, wherein the additional steps comprises: purifying and drying the nanoparticle obtained in the process as defined above or below.

The water-dispersible single-chain polymeric nanoparticle obtainable by a process as defined above in the first aspect of the invention is also part of the invention. For the purposes of the invention the expressions "obtainable", "obtained" and equivalent expressions are used interchangeably, and in any case, the expression "obtainable" encompasses the expression "obtained".

The third aspect of the invention relates to a water-dispersible conjugate, which comprises the water-dispersible single-chain polymeric nanoparticle as defined above in the first and second aspect of the invention and at least an active agent. The structure of the water-dispersible single-chain polymeric nanoparticle is advantageous for their versatility and multifunctionality which allows the loading of a huge range of active agents. Additionally, the particle size and polydispersity of the nanoparticles obtained by the process of the invention is also advantageous because allows obtaining water-dispersible conjugates having the suitable physical and chemical properties for being used in biomedicine.

These active agents can be covalently bound directly or by one or two linkers to the backbone; or alternatively they can be non-covalently bound to the backbone. In an embodiment, optionally in combination with one or more features of the various embodiments described above or below, the active agent is selected from the group consisting of active ingredient, and an imaging agent agent.

In an embodiment, optionally in combination with one or more features of the various embodiments described above or below, the active agent is an active ingredient; preferably the active ingredient is selected from small agents (i.e. pharmaceutical active ingredients) to biomolecules (i.e. peptides, proteins, and nucleic acids). Examples of active ingredient includes, but is not limited to, antibody, antigen, peptide, oligosaccharide, double stranded oligonucleotide (DNA) and siRNA.

The process for preparing a water-dispersible conjugate as defined above is also part of the invention.

In an alternative embodiment, optionally in combination with one or more features of the various embodiments described above or below, the process comprises putting in contact the water-dispersible single-chain polymeric nanoparticles of the present invention with the active agent as defined above to obtain a water-dispersible conjugate.

In an alternative embodiment, optionally in combination with one or more features of the various embodiments described above or below, the process for preparing the water-dispersible conjugate comprises carrying out the process of the first aspect of the invention with a polymer-active agent.

In an embodiment, optionally in combination with one or more features of the various embodiments described above or below, the process for preparing the water-dispersible conjugate, which comprises crosslinking a polymer-active agent with a homobifunctional crosslinking agent, further comprises a previous step of putting in contact the polymer with the active agent as defined above to obtain a polymer-active agent. Therefore, the process comprises putting in contact a polymer having a solubility equal to or higher than 100 mg per litre of water, and an amount of complementary reactive groups comprised from 5 to 60 molar % of the total amount of monomer units present in the polymer chain with an active agent to obtain a polymer-active agent; and crosslinking the polymer-active agent obtained in the previous step with a homobifunctional crosslinking agent having crosslinkable groups; by (a) Adding an aqueous solution of the polymer-active agent to an aqueous solution of the homobifunctional crosslinking agent at an addition rate that allows having during the addition of the polymer-active agent a concentration of the crosslinkable groups of the polymer-active agent in the solution of the homobifunctional crosslinking agent comprised from $10^{-3}$ to $10^{-7}$ molar, or alternatively, (a') Adding an aqueous solution of the homobifunctional crosslinking agent to an aqueous solution of the polymer-active agent at an addition rate that allows having during the addition of the homobifunctional crosslinking agent a concentration of the homobifunctional crosslinking agent in the solution of the polymer-active agent comprised from $10^{-3}$ to $10^{-7}$ molar; at a temperature comprised from 20 to 25° C. in the absence of a catalyst; to obtain a water-dispersible conjugate of the present invention.

In an embodiment, optionally in combination with one or more features of the various embodiments described above or below, the process for preparing the water-dispersible conjugate, which comprises crosslinking a polymer-active agent with a homobifunctional crosslinking agent, further comprises a previous step of preparing the polymer-active agent by polymerising the corresponding monomer units of the polymer in the presence of the active agent to obtain a polymer-active agent as defined above. Therefore, the process comprises polymerising the corresponding monomer units in the presence of the active-agent to obtain a polymer-active agent having an amount of complementary reactive groups comprised from 5 to 60 molar % of the total amount of monomer units present in the polymer chain; and crosslinking the polymer-active agent obtained in the previous step with a homobifunctional crosslinking agent having crosslinkable groups; by (a) Adding an aqueous solution of the polymer-active agent to an aqueous solution of the homobifunctional crosslinking agent at an addition rate that allows having during the addition of the mixture of the polymer-active agent a concentration of the crosslinkable groups of the polymer-active agent in the solution of the homobifunctional crosslinking agent comprised from $10^{-3}$ to $10^{-7}$ molar, or alternatively, (a') Adding an aqueous solution of the homobifunctional crosslinking agent to an aqueous solution of the polymer-active agent at an addition rate that allows having during the addition of the homobifunctional crosslinking agent a concentration of the homobifunctional crosslinking agent in the solution of the polymer-active agent comprised from $10^{-3}$ to $10^{-7}$ molar; at a temperature comprised from 20 to 25° C. in the absence of a catalyst; to obtain a water-dispersible conjugate of the present invention.

In an alternative embodiment, optionally in combination with one or more features of the various embodiments described above or below, the process for preparing the water-dispersible conjugate comprises carrying out the process of the first aspect of the invention with a homobifunctional crosslinking-active agent having crosslinkable groups.

In an alternative embodiment, optionally in combination with one or more features of the various embodiments described above or below, the process for preparing the water-dispersible conjugate, which comprises crosslinking a polymer with a homobifunctional crosslinking-active agent, further comprises a previous step of putting in contact the homobifunctional crosslinking agent with the active agent as defined above to obtain a homobifunctional crosslinking-active agent. Therefore, the process comprises crosslinking a polymer having a solubility equal to or higher than 100 mg per litre of water, and an amount of complementary reactive groups comprised from 5 to 60 molar % of the total amount of monomer units present in the polymer chain with a cross-linking-active agent having crosslinkable groups obtained in the previous step; by (a) Adding an aqueous solution of the polymer to an aqueous solution of the homobifunctional crosslinking-active agent at an addition rate that allows having during the addition of the polymer a concentration of the crosslinkable groups of the polymer in the solution of the homobifunctional crosslinking-active agent comprised from $10^{-3}$ to $10^{-7}$ molar, or alternatively, (a') Adding an aqueous solution of the homobifunctional crosslinking-active agent to an aqueous solution of the polymer at an addition rate that allows having during the addition of the homobifunctional crosslinking-active agent a concentration of the homobifunctional crosslinking-active agent in the solution of the polymer comprised from $10^{-3}$ to $10^{-7}$ molar; at a temperature comprised from 20 to 25° C. in the absence of a catalyst to obtain a water-dispersible conjugate of the invention.

The water-dispersible conjugate of the present invention can be in form of a pharmaceutical or diagnostic composition, which is also part of the invention. Thus, the fourth aspect of the invention relates to a pharmaceutical or diagnostic composition which comprises the water-dispersible conjugate of the present invention, together with one or more appropriate pharmaceutically, or diagnostically acceptable excipients or carriers. Pharmaceutical or diagnostic compositions can be in form of compositions for parenteral administration (intramuscular, subcutaneous or intravenous), enteral administration (oral or rectal) or topical administration (dermal, mucosal or inhaled).

The above mentioned composition can be prepared according to well known methods in the state of the art. The appropriate pharmaceutically or diagnostically acceptable excipients or carriers, and their amounts, can readily be determined by those skilled in the art according to the type of formulation being prepared.

The water-dispersible conjugate of the present invention can be in form of a kit, which is also part of the invention. Thus, the fifth aspect of the invention relates to kit comprising the water-dispersible conjugate as defined above. In an embodiment, the kit further comprises suitable means and/or instructions. In an alternative embodiment, the kit further comprises a solid support, solvents, reagents and/or buffers.

The water-dispersible single-chain polymeric nanoparticles of the present invention are intermediates for the preparation of the water-dispersible conjugate of the present invention. Therefore, The water-dispersible single-chain polymeric nanoparticles of the invention are also useful as carriers for active agents.

The water-dispersible conjugate of the invention which comprises one or more active ingredients are useful in therapy. It also relates to a method for the prophylaxis and/or treatment of a disease which comprises administering to mammals in need of such treatment an effective amount of the water-dispersible conjugate of the present invention, together with one or more appropriate pharmaceutically acceptable excipients or carriers.

In an embodiment, optionally in combination with one or more features of the various embodiments described above or below, the water-dispersible conjugate is that wherein the active agent is an imaging agent. The term "imaging agent" refers to any substance that is used as a label or enhances specific structures in any imaging technique. In an embodiment, the imaging agent is selected from the group consisting of fluorescent agent, contrast agent and radioimaging agent. Examples of imaging agents appropriate for the present invention include, but are not limited to, transition metals and radioactive transition metals chelated to chelating agents, for instance DTPA (diethylene triamine pentaacetic acid), DOTA (1,4,7,10-Tetraazacyclododecane-1,4, 7,10-tetraacetic acid) or NOTA (1,4,7-Triazacyclononane-1, 4,7-triacetic acid), fluorescein, rhodamine, and cyane 5,5.

In an embodiment, optionally in combination with one or more features of the various embodiments described above or below, the water-dispersible conjugate is that wherein the imaging agent is a "contrast agent". The term "contrast agent" refers to agents that accentuate certain structures that would otherwise be hard to see by usual techniques.

Other aspect of the invention relates to the use of the water-dispersible conjugate as an imaging agent when the active agent is an imaging agent.

In an embodiment, the water-dispersible conjugate is used as an imaging agent in detection assays. An appropriate detection assay can comprise: (a) putting into contact the water-dispersible conjugate of the invention having a active agent capable of specifically binding to a target agent with the target agent present in a sample to be tested for an appropriate period of time that allows the binding; and optionally (b) identifying and/or quantifying the target agent. Suitable test samples for the present invention can be serum, plasma, urine, and cephaloraquideum liquid.

In an embodiment, the water-dispersible conjugate is used as an imaging agent in detection assays. An appropriate detection assay can comprise: (a) putting into contact the water-dispersible conjugate of the invention having an active agent capable of specifically binding to a target agent with the target agent present in a subject for an appropriate period of time to allow circulating the water-dispersible conjugate to the target site; and optionally (b) identifying and/or quantifying the target agent. In a particular embodiment the identification and/or quantification of the target agent is carried out by methods well known in the art. Suitable methods for identification and/or quantification can be fluorescence, surface plasmon resonance, and colorimetry.

The detection assay as defined above can be used for diagnostic purposes where the present or an amount of the target agent can be correlated with a specific disease or condition. Thus, other aspect of the invention relates to the water-dispersible conjugate, which comprises one or more imaging agents for use in diagnostics. This aspect could be formulated as a method for the diagnosis of a disease in a subject, the method comprises administering to said subject an effective amount of the water-dispersible conjugate having one or more imaging agents as defined above to the subject. This aspect could also be formulated as a method for the diagnosis of a disease in an isolated sample of a subject, the method comprises administering to said subject an effective amount of the water-dispersible conjugate having one or more imaging agents as defined above to the isolated sample of the subject. The detection of these imaging agents can be carried out by well known techniques such as imaging diagnostic techniques. Examples of imaging diagnostic techniques suitable for the present invention include, but are not limited to magnetic resonance imaging (MRI), X-ray, positron emission tomography (PET), single-photon emission computed tomography (SPECT), fluorescence microscopy, and in vivo fluorescence.

Throughout the description and claims the word "comprise" and variations of the word, are not intended to exclude other technical features, additives, components, or steps. Furthermore, the word "comprise" encompasses the case of "consisting of". Additional objects, advantages, and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

The following abbreviations are used in the below examples:
PBS: Phosphate Buffered Saline
EDC: 3-(Ethyliminomethyleneamino)-N,N-dimethylpropan-1-amine
MES: 2-[N-morpholino]ethanesulfonic acid)
NHS: (N-hydroxysucinimide)
THF: tetrahydrofurane
TFA: trifluoroacetic acid
DMSO: dimethylsulfoxide
PEG: polyethylenglycol
PDI: polydispersity index
Cy5.5: cyanine5.5 NHS ester
DLS: dynamic light scattering
SEC: size exclusion chromatography
ICP: inductively coupled plasma
MWCO: molecular weight cut-off
1. Particles
General Reference Procedure The polymer having a concentration comprised from 0.005-0.05 M of the crosslinkable groups is dissolved in an aqueous solution at temperature of 20-25° C., at an appropriate pH and ionic strength according to the click chemistry involved. The homobifunctional crosslinking agent is dissolved in an aqueous solution at room temperature in a concentration comprised from 0.05-0.5 M at a pH and ionic strength according to the click chemistry involved.

The aqueous solution of the homobifunctional crosslinking agent is added to the aqueous solution of the polymer in a slow, controlled and continuous manner to the aqueous solution of the polymer under vigorous stirring at room temperature. The addition rate of the aqueous solution of the homobifunctional crosslinking agent to the polymer is adjusted to obtain a constant ultradiluted concentration of $10^{-5}$ M of the homobifunctional crosslinking agent in the polymer solution. Optionally, the possible unreacted motifs of the polymer can be quenched using the most suitable molecules.

Then, the solution is dialyzed until the unreacted linkers or quenching molecules are out of the membrane; and finally, the resulting aqueous solution is dry (by freeze-drying) to obtain the particle as a solid compound Example 1: Polymethacrylic Acid (PMAAc) Based Single Chain Polymer Nanoparticles (See FIG. 1)

Figure 1:
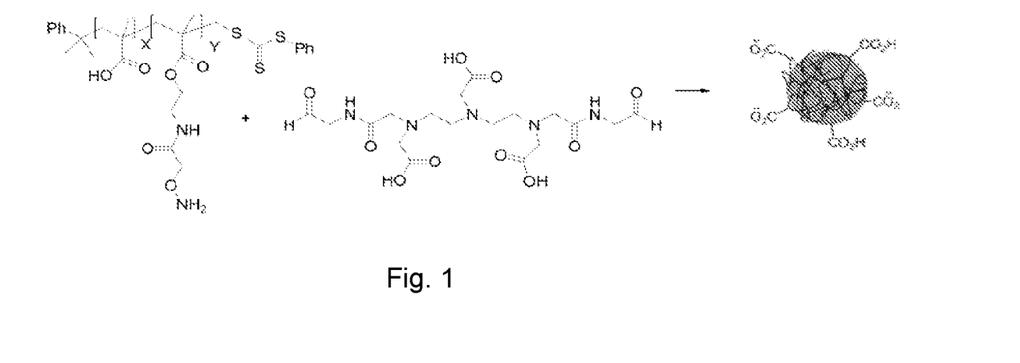
FIG. 1 shows a schematic general route of synthesis of the polymethacrylic acid (PMAAc) based single chain polymer nanoparticles of Example 1 of the present invention.

1A
The homobifunctional crosslinking agent (5,8-bis(carboxymethyl)-2-(2-(2,2-dimethoxyethylamino)-2-oxoethyl)-13-methoxy-10-oxo-14-oxa-2,5,8,11-tetraazapentadecane-1-carboxylic acid) (65 mg; 0.115 mmol) and HCl (5M) (0.46 mL) were mixed and stirred at room temperature for 30 minutes. After that time, pH of the mixture was carefully adjusted to pH 6 with NaOH (aq.). If needed, water was added to complete a total volume of 0.7 mL (Final concentration (0.16M). This solution was used without further purification.

The starting polymer was deprotected from a tert-butyl methacrylate based copolymer (MW around 65000 (using a poly(methyl methacrylate) calibration curve in THF at 40° C.) and polydispersity index (PDI) of 1.44 (THF at 40° C.). The deprotection was performed by treatment with an excess of TFA (5 mL) in 15 mL of dichloromethane/H2O (9/1 v/v) of 1 g of copolymer. The resulting precipitate was washed with dichloromethane and dried under vacuum. The crude deprotected polymer (100 mg) wherein x is 0.83, and y is 0.17 was dissolved in water (1 mL) adding NaOH aq up to pH>12. After a few minutes, the pH of the resulting clear solution (pH 13) was carefully adjusted to 6 with HCl. Water was added to have a final volume of 6.5 mL.

Afterwards the crosslinking agent solution was added to the polymer solution at a rate of 1 mL/h at a temperature of 20-25° C. and was kept stirring for 16 h.

The solution was then precipitated in acetone (130 mL) and a white solid was obtained. The precipitate was afterwards centrifuged and dried in a fume cupboard to remove the acetone traces. Finally the solid was redissolved in water and freeze-dried to obtain 800 mg of nanoparticles with a size of around 23 nm in DLS (in PBS at 25° C.) and a PDI of 1.58 in SEC (phosphate buffer+0.1M NaNO$_3$, pH=6.3, T=40° C.).

1B
The homobifunctional crosslinking agent (5,8-bis(carboxymethyl)-2-(2-(2,2-dimethoxyethylamino)-2-oxoethyl)-13-methoxy-10-oxo-14-oxa-2,5,8,11-tetraazapentadecane-1-carboxylic acid) (65 mg; 0.115 mmol) and HCl (5M) (0.46 mL) were mixed and stirred at room temperature for 30 minutes. After that time, pH of the mixture was carefully adjusted to pH 6 with NaOH (aq.). If needed, water was added to complete a total volume of 0.7 mL Final concentration (0.16M). This solution was used without further purification.

The starting polymer was deprotected from a tert-butyl methacrylate based copolymer (MW around 65000 (using a poly(methyl methacrylate) calibration curve in THF at 40° C.) and polydispersity index (PDI) of 1.44 (THF at 40° C.). The deprotection was performed by treatment with an excess of TFA (5 mL) in 15 mL of dichloromethane/H2O (9/1 v/v) of 1 g of copolymer. The resulting precipitate was washed with dichloromethane and dried under vacuum. The crude deprotected polymer (100 mg) wherein x is 0.83, and y is 0.17 was dissolved in water (1 mL) adding NaOH aq up to pH>12. After a few minutes, the pH of the resulting clear solution (pH 13) was carefully adjusted to 6 with HCl. Water was added to have a final volume of 6.5 mL.

Afterwards, the crosslinking agent 0.16M solution (0.38 mL) was added to the polymer solution at a rate of 0.12 mL/h and at a temperature of 20-25° C. The solution was stirred for 48 h. Picoline borane complex (13.8 mg) was then added and, after 12 hours, the reaction crude was loaded into a 3500 MWCO membrane and dialysed against pure water until conductivity was reduced to around 1 μS/cm. The aqueous solution so obtained (21 mL) was stored in the fridge at 4° C. at a concentration of 3.7 mg/mL. The nanoparticles obtained showed a size of 11 nm measured by DLS (in PBS measured at 25° C.).

Example 2: Fluorescein Labelled Poly(N,N-dimethylaminoethyl) methacrylate (PDMAEMA) Based Single Chain Polymer Nanoparticles 2A. Preparation of Poly(N,N-dimethylaminoethyl) methacrylate (PDMAEMA) Based Single Chain Polymer Nanoparticles.

The particles of Example 2 were carried out following the process described in Example 1 using the poly[N,N-dimethyl-2-aminoethylmethacrylate$_{0.87}$-co-(2-(2-(aminoxy)acetamido)ethylmethacrylate$_{0.13}$] as a polymer (300 mg, 0.14 mmol of reactive crosslinkable group MW around 53000 (using a poly(methyl methacrylate) calibration curve in THF at 40° C.)), and 5,8-bis(carboxymethyl)-2-(2-(2,2-dimethoxyethylamino)-2-oxoethyl)-13-methoxy-10-oxo-14-oxa-2,5,8,11-tetraazapentadecane-1-carboxylic acid (57 mg, 0.098 mmol) as a homobifunctional crosslinking agent. The nanoparticles obtained showed a size of around 15 nm in DLS (in PBS at 25° C.) and a PDI of 1.22 in SEC (THF at 40° C.).

2B. Fluorescein Labelling of Poly(N,N-dimethylaminoethyl) methacrylate (PDMAEMA) Based Single Chain Polymer Nanoparticles.

Nanoparticles obtained from Example 2 (20 mg, 0.1 mmol of main monomer) were dissolved in 400 μl of water and the solution was shaken (800 rpm) at 65° C. After 10 minutes 6-bromohexanoic acid (1.95 mg, 0.01 mmol) dissolved in DMSO (concentration of 50 mg/mL) was added to the mixture and was left shaking at 65° C. for 36 h. The sample thus obtained was filtered by centrifugation (10,000 rpm, 30 min) in VIVASPIN 6 tube (cutoff 3 KDa) (previously washed with water twice), and it was washed three times with water/DMSO 95:5 (3×1 mL).

Particles in the filter were collected with 1 ml of water/DMSO (3:1) and EDC (1.92 mg, 0.01 mmol) was added. After 10 min, NHS (1.15 mg, 0.01 mmol) was added and the solution was left stirring at 40° C. for 20 min. Then fluorescein-5-thiosemicarbazide (0.33 mg, 0.001 mmol) dissolved in DMSO (concentration of 50 mg/mL) was added and the mixture was left stirring at 40° C. for 16 h. The solution was then dialyzed in the dark (MWCO=3500) against pure water until conductivity was reduced to around 1 μS/cm and the product was freeze-dried to obtain an orange powder (13.7 mg).

Example 3: Dextran (DXT) Based Single Chain Polymer Nanoparticles (See FIG. 2)

Figure 2:
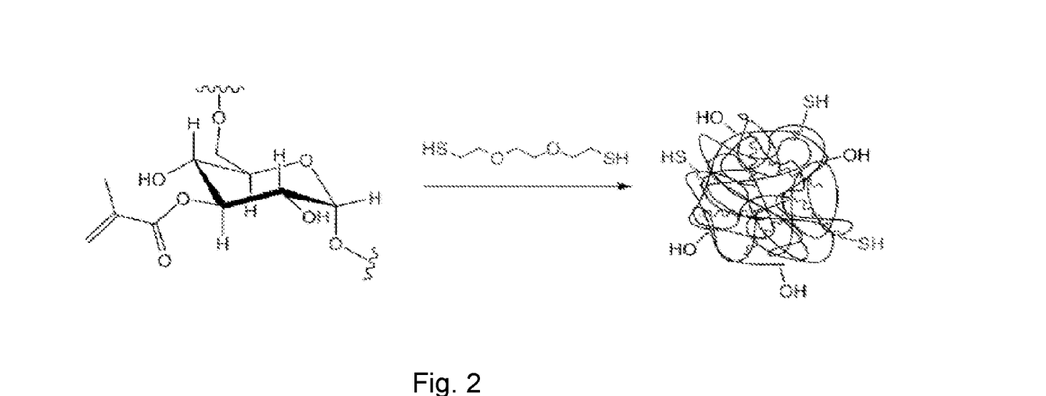
FIG. 2 shows a schematic general route of synthesis of the dextran (DXT) based single chain polymer nanoparticles of Example 3 of the present invention.

3A

The homobifunctional crosslinking agent (20 mg, 0.112 mmol) was dissolved in 0.73 mL of a mixture of PBS/MeOH 1:1 and the pH was adjusted to 9.5.

The polymer based on Dextran (300 mg, 0.39 mmol of crosslinkable groups) was also dissolved in PBS (25 mL) and pH was adjusted to 9. Afterwards the crosslinking agent solution was added to the polymer solution at a rate of 0.02 mL/h ($7 \times 10^{-5}$ mM/min) and was kept stirring for 36.5 h of addition.

The solution thus obtained was then dialyzed (MWCO=1000 Da) against pure water first until the conductivity is reduced to around 1 μS/cm, and pure water adjusted to pH 9 using NaOH afterwards (2 water changes). Finally the resulting aqueous solution was freeze-dried to obtain 279.9 mg of nanoparticles as a white solid. The nanoparticles obtained showed a size of around 18 nm in DLS (in PBS measured at 25° C.) and a PDI of 2.14 in SEC (phosphate buffer+0.1M NaNO$_3$, pH=6.3, T=40° C.).

3B

The homobifunctional crosslinking agent (12 mg, 0.067 mmol) was dissolved in 0.43 mL of a mixture of PBS/MeOH 1:1 and the pH was adjusted to 9.5. The polymer based on Dextran (300 mg, 45 molar % of crosslinkable groups, was also dissolved in PBS (25 mL) and pH was adjusted to 9. Afterwards the crosslinking agent solution was added to the polymer solution at a rate of 0.02 mL/h ($7 \times 10^5$ mM/min) and was kept stirring for 36.5 h of addition. Ellman's test was performed to ensured the absence of the thiol reactive groups.

The solution thus obtained was then dialyzed (MWCO=1000 Da) against pure water first until the conductivity is reduced to around 1 μS/cm. Finally the resulting aqueous solution was freeze-dried to obtain nanoparticles as a white solid. The nanoparticles obtained showed a size of 9 nm measured by DLS.

3C

The homobifunctional crosslinking agent (16 mg, 0.09 mmol) was dissolved in 0.57 mL of a mixture of PBS/MeOH 1:1 and the pH was adjusted to 9.5. The polymer based on Dextran (300 mg, 35 molar % of crosslinkable groups, was also dissolved in PBS (25 mL) and pH was adjusted to 9. Afterwards the crosslinking agent solution was added to the polymer solution at a rate of 0.02 mL/h ($7 \times 10^{-5}$ mM/min) and was kept stirring for 36.5 h of addition. Ellman's test was performed to ensured the absence of the thiol reactive groups.

The solution thus obtained was then dialyzed (MWCO=1000 Da) against pure water first until the conductivity is reduced to around 1 μS/cm. Finally the resulting aqueous solution was freeze-dried to obtain nanoparticles as a white solid. The nanoparticles obtained showed a size of 10 nm measured by DLS.

3D

The homobifunctional crosslinking agent (20 mg, 0.11 mmol) was dissolved in 0.73 mL of a mixture of PBS/MeOH 1:1 and the pH was adjusted to 9.5. The polymer based on Dextran (300 mg, 55 molar % of crosslinkable groups, was also dissolved in PBS (25 mL) and pH was adjusted to 9. Afterwards the crosslinking agent solution was added to the polymer solution at a rate of 0.02 mL/h ($7 \times 10^{-5}$ mM/min) and was kept stirring for 36.5 h of addition. Ellman's test was performed to ensured the absence of the thiol reactive groups.

The solution thus obtained was then dialyzed (MWCO=1000 Da) against pure water first until the conductivity is reduced to around 1 µS/cm. Finally the resulting aqueous solution was freeze-dried to obtain nanoparticles as a white solid. The nanoparticles obtained showed a size of 6 nm measured by DLS.

2. Water-Dispersible Conjugates

Example 4: Gadolinium-Conjugate

Particles obtained in Example 2 (62 mg, 0.022 mmol of linker) were dissolved in water (1 mL) and the pH was adjusted to 6 using HCl0.1M. Then a solution of $GdCl_3.6H_2O$ (20.5 mg in 1.25 mL, 0.055 mmol) was added slowly and the mixture was left stirring at room temperature for 16 hours. Finally, the sample was dialyzed (MWCO=1000) against pure water until the conductivity is reduced to around 1 µS/cm, and the resulting aqueous solution was freeze-dried to obtain 60 mg of the nanoparticles as a white solid, with a size of around 25 nm in PBS measured in DLS, with the Gd quantity incorporated being around 2.5 weight % measured by inductively coupled plasma (ICP). Relaxivity values measured in a Minispec TD-NMR spectrometer of 60 MHz were $R_1=8.4$ $s^{-1}mM^{-1}$ and $R_2=10.5$ $s^{-1}$ $mM^{-1}$ in PBS.

Example 5: MALEIMIDE-NODA-GA-Conjugate

Particles obtained in Example 1A (50 mg, approx. 0.39 mmol of acid units) were dispersed in water (1 mL). EDC.HCl (75 µL of a solution 100 mg/mL in water, 0.039 mmol) and NHS (45 µL of a solution 100 mg/mL in water, 0.039 mmol) were added and the mixture was shaken (900 rpm) at 40° C. for 2 h 30 min. After that time, cysteamine (30 µL of a solution 100 mg/mL in water, 0.039 mmol) was added and it was shaken (900 rpm) at 40° C. for 16 h.

The sample thus obtained was filtered by centrifugation (10,000 rpm, 30 min) in VIVASPIN 20 tube (cutoff 5 KDa) (previously washed with water twice), and it was washed twice with water (2×8 mL).

Particles in the filter were collected with water (2 mL) and tris(2-carboxyethyl)phosphine (TCEP) (100 mg, 0.39 mmol) was added, and a white precipitate appeared. Then, pH was adjusted pH was adjusted to 5-6 using NaOH 5M (once pH was 5 the precipitate disappeared).

MALEIMIDE-NODA-GA (30 µL of a solution 100 mg/mL in DMSO, 0.0039 mmol) was added and the reaction mixture was stirred at 40° C. for 3 hours. After that time, bromoethanol (16.4 µL, 0.195 mmol) was added and it was stirred at 40° C. for 16 h. Finally the product was dialyzed against basic water (pH 9) for 2 days (membrane cutoff: 1 KDa, 3 water changes). It was freeze-dried to obtain 31 mg of a nanoparticle having a particle size of around 54 nm measured in DLS (in PBS at 25° C.).

Example 6: $NH_2$-NODA-GA-Conjugate

Particles obtained in Example 1B (60 mg) were dispersed in H2O (1 mL) and pH was adjusted to pH 8-8.5 by NaOH addition. H2O was added until reaching a final volume of 2 mL. Then, 325 µL of a solution (100 mg/mL) of DMTMM-.HCl in H2O was added, and the mixture was stirred at room temperature for 20 min. Then, 235 µL of a solution (25 mg/mL) of NODA-GA-NH2 in DMSO was added. The reaction mixture was stirred at room temperature overnight and then dialyzed against water at pH ~7 for 3 days (3 water changes per day) at 25° C. (MWCO: 3500 Da). Functionalized nanoparticles were stored in solution (Final volume 6.2 mL; c=4 mg/mL). The nanoparticles obtained showed a size of around 18 nm in DLS (in PBS measured at 25° C.).

Example 7: Double Stranded Oligonucleotide-Conjugate

Double Stranded Oligonucleotide:

```
SEQ ID NO. 1:
3'-TTAAAAAGAGGAAGAAGTCTA-5'

SEQ ID NO. 2:
5'-TTTTTCTCCTTCTTCAGATTT-3'
```

Particles obtained in Example 2, and the double strand oligonucleotide as defined above comprising 23 bases and having a MW=12829.6 (ordered to Microsynth) are dissolved separately in PBS to a concentration of 60 µM. Dividing the final volume in 3 equal parts, one part is the solution of the double stranded oligonucleotide and the other two are the particle solution. The particle solution (⅔ of the final volume) is put in agitation at about 600 rpm in a thermoblock at 37° C. While the particle solution is in agitation the double stranded oligonucleotide solution is added slowly, and as soon as it is added the mixture is vortexed for at least 10 seconds. After that the solution is left resting for at least 30 min before use. The water-dispersible conjugates obtained (for 20:1 N/P) were of around 20 nm in size measured in DLS (in PBS at 25° C.).

Example 8: Octreotide/Cyane 5.5/PEG-Conjugate

To a solution of particles obtained in Example 2 (30 mg, approx. 0.077 mmol of acid units) in MES buffer at pH=6 (1.5 mL), EDC (14.76 mg, 0.077 mmol) was added. After 10 min, NHS (8.85 mg, 0.077 mmol) was added and the reaction was maintained stirring at 40° C. for 3 hours.

Then, Octreotide (Sigma-Aldrich) was added (0.0077 mmol, 10.85 mg) in a DMSO solution (108.5 µL of a 100 mg/mL solution) and the pH was adjusted to 7.4 using NaOH. After 3 hour stirring at 40° C., Cy5.5 was added (0.0015 mmol, 1.01 mg) in water (10 µL of a 100 mg/mL solution) and the mixture was covered from light. After one hour, PEG 750 was incorporated to the reaction (0.03 mmol, 23.24 mg) and left stirring at 40° C. for 16 h. The solution was then dialyzed in the dark (MWCO=3500) against pure water until conductivity was reduced to around 1 µS/cm and the product was freeze-dried to obtain a green powder (15.2 mg). The percentage of the incorporated molecules was as follows: -Octreotide 3.2 weight %; Cy5.5 0.2 weight %; PEG 750 1% mol.

3. Internalization Study

3A. Flow Cytometry (i) Method

Nanoparticle uptake studies with flow cytometry were carried out using HepG2 cells (human hepatocarcinoma). The apparatus used is a FACSCanto II from Bioscience with three lasers: violet (405 nm), blue (488 nm) and red (633 nm). HepG2 was cultured in Dulbecco's modified Eagle's medium (DMEM) with 10% fetal bovine serum (FBS), 1000 U penicillin, and 10 mg/mL streptomycin at 37° C. and 5% CO2. When the cell confluence was around 70%, the cells were trypsinized and resuspended in culture medium. A total of 300000 cells were seeded into each well of a 24-well culture plate.

Fluorescein labelled nanoparticles of Example 2 were added into the culture medium 24 h later in the concentrations as defined in Table 1. After cultured for 1, 2, 4, 8 and 24 hours the cells were washed twice with PBS, trypsinized, and studied by flow cytometry. The uptake ratio was calculated from the dotplot graph of forward scattering (FCS) versus fluorescence intensity (PE-A). Data were analyzed with the WinMDI program.

(ii) Sample

Nanoparticle: Fluorescein labelled poly(N,N-dimethylaminoethyl) methacrylate (PDMAEMA) based single chain polymer nanoparticles of Example 2 of the present invention.

Concentrations (μg/mL): 10, 50 and 100.

(iii) Results

Table 1 shows the uptake rates of the nanoparticles of the present invention at several concentrations and exposure times.

TABLE 1

| UPTAKE RATE Concentration | Time (h) | | | | |
|---|---|---|---|---|---|
| (ug/mL) | 1 | 2 | 4 | 8 | 24 |
| 10 | 8.69 ± 1.14 | 21.27 ± 4.43 | 45.22 ± 4.69 | 78.44 ± 3.89 | 98.73 ± 0.17 |
| 50 | 25.07 ± 13.09 | 48.58 ± 24.26 | 78.51 ± 14.93 | 97.73 ± 1.17 | 99.92 ± 0.04 |
| 100 | 38.08 ± 21.30 | 60.60 ± 22.54 | 89.79 ± 6.66 | 99.49 ± 0.30 | 99.93 ± 0.01 |

As it is shown in the uptake rates of Table 1, there is a proportional increase in the absorption of the nanoparticles of the present invention inside the tested cells, even wherein high concentrations of nanoparticles are used (i.e. 100 μg/ml). Particularly, after 4 h of incubation, 90% of the 100 μg/ml of the nanoparticles of the invention were absorbed inside the cells, and after 8 h all the nanoparticles were absorbed by the cells. These results are an indication that the nanoparticles of the invention do not have a significant toxicity and, therefore, the nanoparticles of the present invention are appropriate for their use in the biomedicine field.

3B. Confocal Microscopy (i) Method

Nanoparticle uptake studies with confocal microscopy were carried out using HepG2 cells (human hepatocarcinoma). The apparatus used to image HepG2 cells after incubation with fluorescein labelled nanoparticles is CLSM (Carl-Zeiss LSM 10 META). A total of 100000 cells were seeded in a 3.5 cm culture plate containing a coverslip, which was placed into a 3.5 cm culture plate. After 24 h, the fluorescently fluorescein labelled nanoparticles as defined in Example 2 were added into the culture medium with a final concentration of 50 μg/mL. After incubation for another 4 hours the culture medium was removed and the cells were rinsed three times with sterilized PBS. The cells were subsequently fixed with 3.7% formaldehyde solution in PBS for 30 min and rinsed again. Finally, the cells on these coverslips were observed under CLSM employing a 63× oil immersion objective with a pinhole aperture of 0.75 μm.

(ii) Sample

Nanoparticles: Fluorescein labelled poly(N,N-dimethylaminoethyl) methacrylate (PDMAEMA) based single chain polymer nanoparticles of Example 2 of the present invention.

Concentration (μg/mL): 50.

(iii) Results

Images obtained by confocal microscopy confirmed that the nanoparticles of the present invention were capable of internalizing inside the tested cells. It was possible to visualize the nanoparticles labelled with fluorescein inside the tested cells as green dots.

---

The invention claimed is:

1. A process for preparing a water-dispersible single-chain polymeric nanoparticle, which comprises cross-linking a polymer having a solubility equal to or higher than 100 mg per litre of water, and an amount of complementary reactive groups comprised from 5 to 60 molar % of the total amount of monomer units present in the polymer chain; with a homobifunctional crosslinking agent having crosslinkable groups; by
   (a) Adding an aqueous solution of the polymer to an aqueous solution of the homobifunctional crosslinking agent at an addition rate that allows having during the addition of the polymer a concentration of the crosslinkable groups of the polymer in the solution of the homobifunctional crosslinking agent comprised from $10^{-3}$ to $10^{-7}$ molar; or alternatively,
   (a') Adding an aqueous solution of the homobifunctional crosslinking agent to an aqueous solution of the polymer at an addition rate that allows having during the addition of the homobifunctional crosslinking agent a concentration of the homobifunctional crosslinking agent in the solution of the polymer comprised from $10^{-3}$ to $10^{-7}$ molar;
   at a temperature comprised from 20 to 25° C. in the absence of a catalyst;
   wherein the water-dispersible single-chain polymeric nanoparticle has a particle size comprised from 3 to 30 nm and a polydispersion of the particle equal to the polydispersion of polymer ±20%;
   optionally the process further comprises an additional step of purifying the water-dispersible single-chain polymeric nanoparticle, and
   optionally the process further comprises an additional step of drying the water-dispersible single-chain polymeric nanoparticle.

2. The process according to claim 1, wherein the nanoparticle has a percentage of intra-molecular crosslinking comprised from 3 to 45 molar % of the total amount of monomer units present in the polymer chain.

3. The process according to claim 1, wherein the process further comprises a previous step of submitting a polymer with protected complementary reactive groups to a deprotection reaction to yield the polymer having complementary reactive groups.

4. The process according to claim 1, wherein the complementary reactive group of the polymer is a —O—NH$_2$ group, the crosslinkable group of the homobifunctional crosslinking agent is a —CHO group, and the process is carried out at a pH comprised from 5 to 7; or alternatively,
   wherein the complementary reactive group of the polymer is a —CHO group, the crosslinkable group of the homobifunctional crosslinking agent is a —O—NH$_2$ group, and the process is carried out at a pH comprised from 5 to 7.

5. The process according to claim 1, wherein the complementary reactive group of the polymer is a —O—C(=O)—C(=CH$_2$)—CH$_3$ group, the crosslinkable group of the homobifunctional crosslinking agent is a —SH group, and the process is carried out at a pH equal to or higher than 8; or alternatively,
   wherein the complementary reactive group of the polymer is a —SH group, the crosslinkable group of the homobifunctional crosslinking agent is a —O—C(=O)—C(=CH$_2$)—CH$_3$ group, and the process is carried out at a pH equal to or higher than 8.

6. A water-dispersible single-chain polymeric nanoparticle, obtainable by the process as defined in claim 1.

7. A water-dispersible conjugate, which comprises the water-dispersible single-chain polymeric nanoparticle as defined in claim 6 and at least an active agent.

8. The water-dispersible conjugate according to claim 7, wherein the active agent is selected from an active ingredient and an imaging agent.

9. The water-dispersible conjugate according to claim 8, wherein the active agent is an imaging agent.

10. A pharmaceutical or diagnostic composition which comprises the water-dispersible conjugate as defined in claim 7, together with one or more appropriate pharmaceutically or diagnostically acceptable excipients or carriers.

11. A kit comprising the water-dispersible conjugate as defined in claim 7.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: oligonucleotide

<400> SEQUENCE: 1
atctgaagaa ggagaaaaat t                                    21

<210> SEQ ID NO 2
<211> LENGTH: 21
<212> TYPE: DNA
<213> ORGANISM: Artificial Sequence
<220> FEATURE:
<223> OTHER INFORMATION: oligonucleotide

<400> SEQUENCE: 2
tttttctcct tcttcagatt t                                    21